(12) United States Patent
Sugiyama et al.

(10) Patent No.: US 6,372,333 B1
(45) Date of Patent: *Apr. 16, 2002

(54) COMPOSITION CONTAINING INORGANIC POROUS CRYSTALS-HYDROPHILIC MACROMOLECULE COMPOSITE AND PRODUCT MADE THEREFROM

(75) Inventors: Kouju Sugiyama; Maki Nakano; Takaaki Utsunomiya; Yoshinobu Fujimoto, all of Osaka (JP)

(73) Assignee: Rengo Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/257,070

(22) Filed: Feb. 24, 1999

Related U.S. Application Data

(63) Continuation-in-part of application No. 09/252,754, filed on Feb. 19, 1999, now abandoned.

(30) Foreign Application Priority Data

Feb. 25, 1998 (JP) .............................................. 10-43534
Feb. 25, 1998 (JP) .............................................. 10-43539
Feb. 25, 1998 (JP) .............................................. 10-43632

(51) Int. Cl.$^7$ .............................................. D21H 11/00
(52) U.S. Cl. .............................. 428/311.71; 428/304.4; 428/311.11; 428/312.2; 428/312.4; 428/312.6; 428/292.1; 442/370; 524/431; 524/432; 524/435; 524/450
(58) Field of Search ........................ 428/292.1, 311.71, 428/304.4, 311.11, 312.2, 312.4, 312.6; 442/370; 524/431, 432, 435, 450

(56) References Cited

U.S. PATENT DOCUMENTS 4,775,585 A  10/1988  Hagiwara et al. ............ 428/323
5,925,308 A * 7/1999  Fewkes et al. ............... 264/623
5,981,052 A  11/1999  Sugiyama ............... 428/311.71

FOREIGN PATENT DOCUMENTS

EP  0 116 865 A1  8/1984
EP  0 826 822  3/1998
WO  WO 92/16291  10/1992

OTHER PUBLICATIONS

*Database WPI*, Section Ch, Week 7949, Abstract Identification No. XP002103627 (1979).
*Patent Abstracts of Japan*, vol. 010, No. 031 (C–327) (1986).
*Database WPI*, Section Ch, Week 8941, Abstract Identification No. XP002103625 (1989).
*Patent Abstracts of Japan*, vol. 014, No. 423 (C–0757) (1990).
*Database WPI*, Section Ch, Week 9223, Abstract Identification No. XP002103626 (1992).
*Database WPI*, Section Ch, Week 9751, Abstract Identification No. XP002103624 (1997).

* cited by examiner

*Primary Examiner*—Terrel Morris
*Assistant Examiner*—John J. Guarriello
(74) *Attorney, Agent, or Firm*—Leydig, Voit & Mayer, Ltd.

(57) ABSTRACT

A composition containing a function improver and an inorganic porous crystals-hydrophilic macromolecule composite wherein the hydrophilic macromolecule contains inorganic porous crystals in its inner matrix, and a product made therefrom The product, textile, nonwoven fabric, paper and laminate obtained from the composition of the present invention come to have high strength in addition to the gas adsorption capability, volatile organic solvent removing capability, noncombustibility, heat insulating property, and heavy metal and radioactive element removing capability that the inorganic porous crystals-hydrophilic macromolecule composite (A) possesses. It is also possible to improve a touch and the like, so that the composition is useful as a material having additional functions.

14 Claims, 5 Drawing Sheets

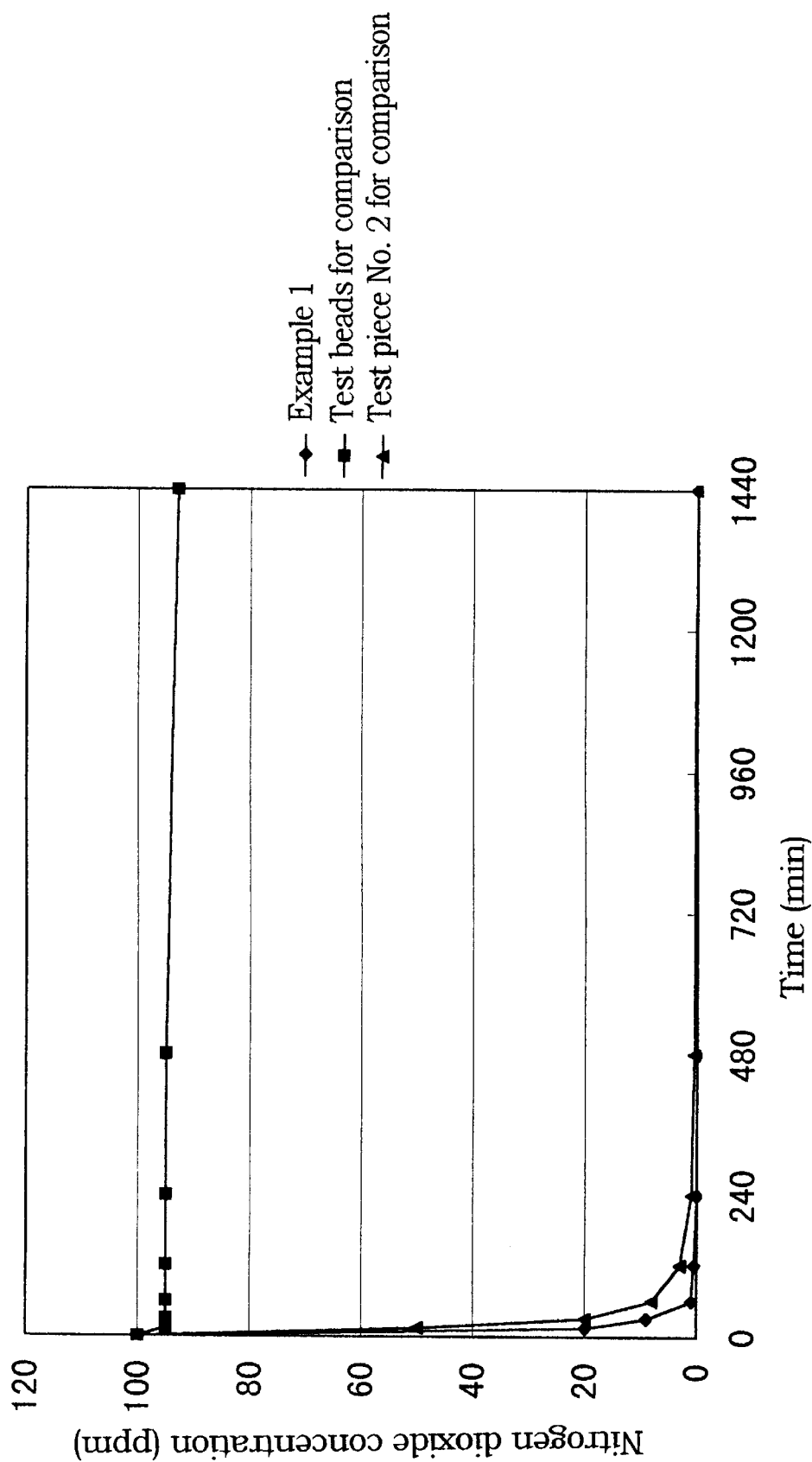

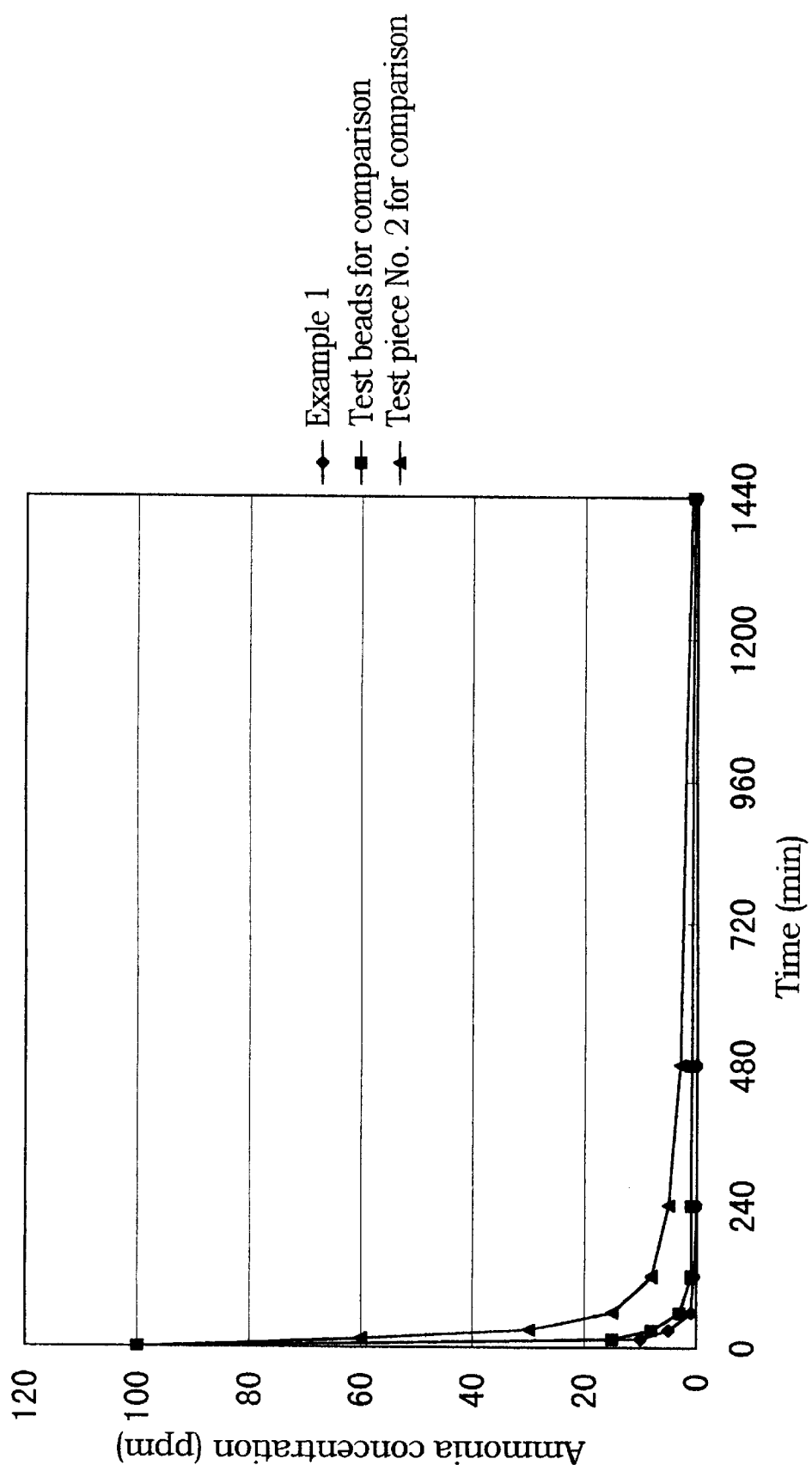

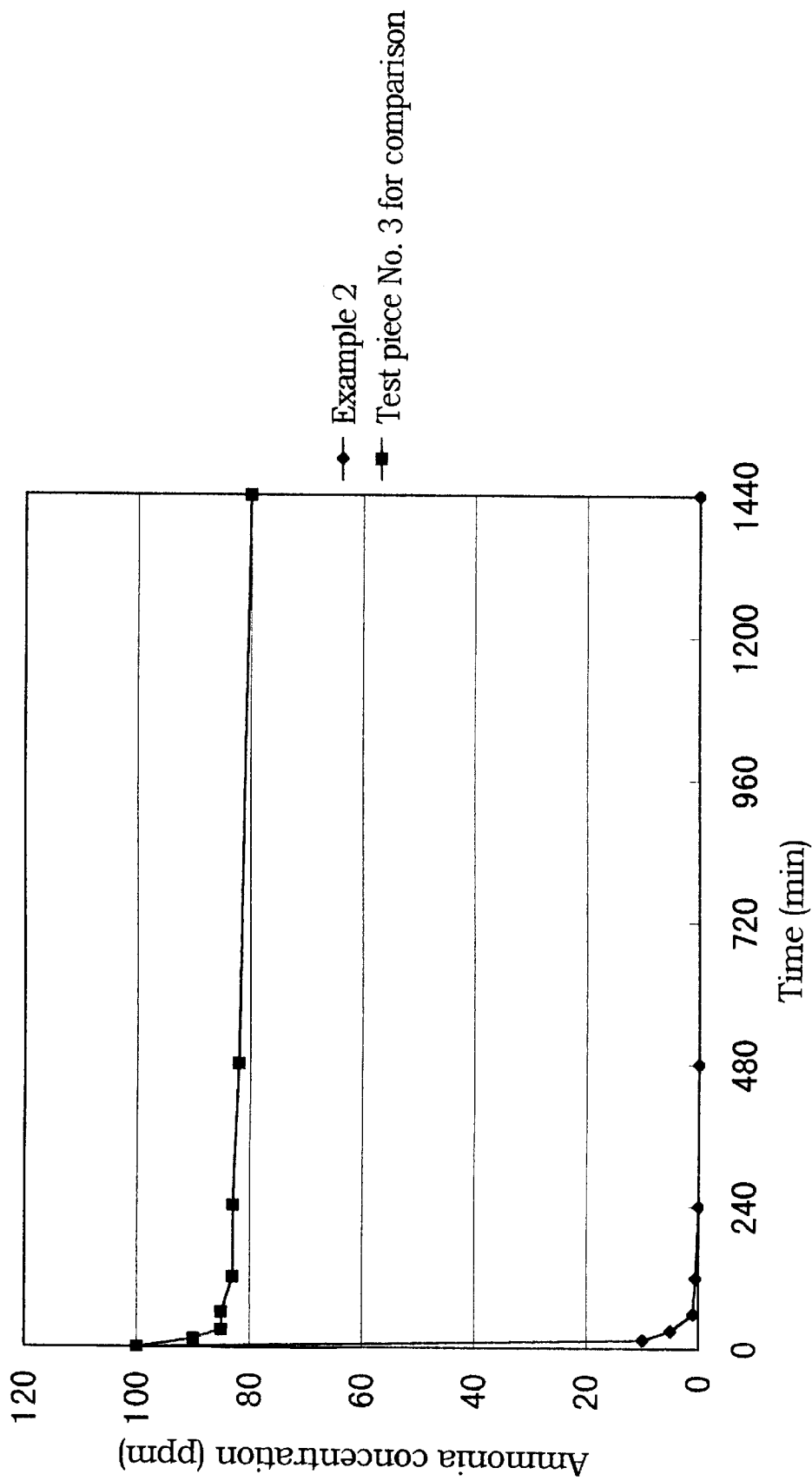

COMPOSITION CONTAINING INORGANIC POROUS CRYSTALS-HYDROPHILIC MACROMOLECULE COMPOSITE AND PRODUCT MADE THEREFROM

This application is a continuation-in-part of Ser. No. 09/252,754 filed Feb. 19, 1999 abandoned.

TECHNICAL FIELD OF THE INVENTION

The present invention relates to a composition comprising a function improver (B) and an inorganic porous crystals-hydrophilic macromolecule composite (A), which is capable of removing bad odor, adsorbing gas and the like, and which is superior in antibacterial property, noncombustibility, heat insulating property, strength and other properties, wherein the hydrophilic macromolecule contains inorganic porous crystals in its inner matrix, and to a product comprising the above-mentioned components (A) and (B).

BACKGROUND OF THE INVENTION

A material obtained by carrying an inorganic compound, such as zeolite and aluminosilica gel, on a hydrophilic macromolecule substrate of cellulose substrate, such as paper and the like, to impart various functions has been known. Such material can be used for various applications since it can remove bad odor, adsorb gas and the like, and shows antibacterial property, noncombustibility and heat insulating property.

Inasmuch as the above-mentioned material is expected to be useful in various applications, one having various high functions, such as higher strength and the like, has been desired to meet the requests of actual end users.

It is therefore an object of the present invention is to provide a material fulfilling such requests, which is an inorganic porous crystals-hydrophilic macromolecule composite having improved functions besides the functions of removing bad odor, adsorbing gas and the like, antibacterial property, noncombustibility, heat insulating property and the like, wherein the hydrophilic macromolecule contains inorganic porous crystals in its inner matrix.

SUMMARY OF THE INVENTION

Such object can be achieved by the present invention described in the following.

The present invention provides the following.
1. A composition comprising (B) a function improver and (A) an inorganic porous crystals-hydrophilic macromolecule composite, wherein the hydrophilic macromolecule contains inorganic porous crystals in its inner matrix.
2. The composition of the above-mentioned (1), wherein the function improver (B) is a carrier capable of solidifying.
3. The composition of the above-mentioned (1), wherein the inorganic porous crystals of the inorganic porous crystals-hydrophilic macromolecule composite (A) are zeolite.
4. The composition of the above-mentioned (1), wherein the inorganic porous crystals hold at least one metal selected from the group consisting of silver, copper, zinc, iron, nickel, cobalt, palladium and platinum.
5. The composition of the above-mentioned (1), wherein the hydrophilic macromolecule is at least one member selected from the group consisting of natural cellulose, regenerated cellulose, bacterial cellulose, chemically-modified cellulose, silk wool, polyacrylamide, polyvinyl alcohol, crosslinked polyvinyl alcohol, chitin, chitosan, ethylene-vinyl acetate copolymer and polyvinyl formal.
6. The composition of the above-mentioned (5), wherein the natural cellulose is at least one member selected from the group consisting of pulp, cotton, hemp and kenaf.
7. The composition of the above-mentioned (5), wherein the chemically-modified cellulose is at least one member selected from the group consisting of ethyl cellulose, hydroxyethyl cellulose, hydroxypropyl cellulose, methyl cellulose, ethyl hydroxyethyl cellulose and carboxymethyl cellulose.
8. A product obtained by solidifying the composition of the above-mentioned (2).
9. A product comprising (A) an inorganic porous crystals-hydrophilic macromolecule composite wherein the hydrophilic macromolecule contains inorganic porous crystals in its inner matrix, and (B) a function improver.
10. The product of the above-mentioned (9), which is a laminate comprising a layer made from the inorganic porous crystals-hydrophilic macromolecule composite (A) and a function improving substrate (B2).
11. The product of the above-mentioned (9), which is a textile, nonwoven fabric or paper comprising a fiber made from the inorganic porous crystals-hydrophilic macromolecule composite (A) and a function improving fiber (B1).
12. The product of the above-mentioned (10), wherein the function improving substrate (B2) comprises at least one member selected from the group consisting of a plastic film, a regenerated cellulose film, a metal foil, a natural fiber, a semisynthetic fiber, a synthetic fiber, a metallic fiber, an inorganic fiber, an active charcoal fiber, an inorganic hardener and an inorganic membrane.
13. The product of the above-mentioned (11), wherein the function improving fiber (B1) comprises at least one member selected from the group consisting of a natural fiber, a chemical fiber and an inorganic fiber.
14. The product of the above-mentioned (9), wherein the inorganic porous crystals are zeolite.
15. The product of the above-mentioned (9), wherein the inorganic porous crystals hold at least one metal selected from the group consisting of silver, copper, zinc, iron, nickel, cobalt, palladium and platinum.
16. The product of the above-mentioned (9), wherein the hydrophilic macromolecule is at least one member selected from the group consisting of natural cellulose, regenerated cellulose, bacterial cellulose, chemically-modified cellulose, silk, wool, polyacrylamide, polyvinyl alcohol, crosslinked polyvinyl alcohol, chitin, chitosan, ethylene-vinyl acetate copolymer and polyvinyl formal.
17. The product of the above-mentioned (16), wherein the natural cellulose is at least one member selected from the group consisting of pulp, cotton, hemp and kenaf.
18. The product of the above-mentioned (16), wherein the chemically-modified cellulose is at least one member selected from the group consisting of ethyl cellulose, hydroxyethyl cellulose, hydroxypropyl cellulose, methyl cellulose, ethyl hydroxyethyl cellulose and carboxymethyl cellulose.

BRIEF DESCRIPTION OF THE DRAWINGS

FIG. 6 is a graph showing nitrogen dioxide removing capability of each test piece in Experiment 1.

FIG. 7 is a graph showing ammonia removing capability of each test piece in Experiment 1.

FIG. 8 is a graph showing ammonia removing capability of each test piece in Experiment 2.

DETAILED DESCRIPTION OF THE INVENTION

Inorganic Porous Crystals

Figure 1:
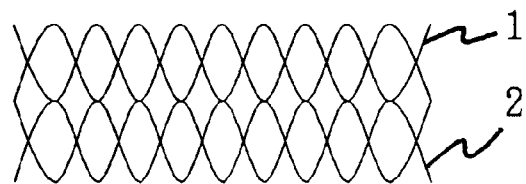
FIG. 1 shows one embodiment of the laminate of the present invention, wherein the inorganic porous crystals-hydrophilic macromolecule composite (A) is an inorganic porous crystals-pulp composite. In the FIG. 1 is a substrate made from a fiber and 2 is a layer made from a fiber of an inorganic porous crystals-pulp composite.

The inorganic porous crystal of the inorganic porous crystals-hydrophilic macromolecule composite (A) to be used in the present invention is, for example, inorganic ion exchange crystal having ion exchange capability or adsorber crystal having adsorption capability in the porous part. It is free of particular limitation as long as it does not dissolve, decompose or disintegrate a hydrophilic macromolecule. For example, zeolite, hydrotalcite, hydroxyapatite, clay minerals and the like can be used.

Of these, zeolite is most preferred in view of its widest uses, with particular preference given to 4A zeolite [$Na_{12}Si_{12}Al_{12}O_{48} \cdot 27H_2O$] for comparatively easy synthesis.

Hydrophilic Macromolecule

The hydrophilic macromolecule of the inorganic porous crystals-hydrophilic macromolecule composite (A) to be used in the present invention is subject to no particular limitation as long as it swells with water. Examples thereof include natural cellulose such as pulp and kenaf, regenerated cellulose (e.g., cellophane, cellulose beads, rayon, cellulose sponge and the like), cotton, bacterial cellulose and cellulose derivatives obtained by chemically-modifying cellulose (e.g., ethyl cellulose, hydroxyethyl cellulose, hydroxypropyl cellulose, methyl cellulose, ethyl hydroxyethyl cellulose and carboxymethyl cellulose, and the like), and natural or artificial hydrophilic macromolecules such as silk wool, hemp, polyvinyl alcohol, crosslinked polyvinyl alcohol, chitin, chitosan, ethylene-vinyl acetate copolymer, polyvinyl formal and the like, highly water-absorbable macromolecule gels such as polyacrylamide and the like, collagen, propolis, urushi, wood powder and the like.

Of these, pulp and regenerated cellulose are preferably used in view of the mode of actual use, price and easy handling.

Inorganic Porous Crystal Hydrophilic Macromolecule Composite (A)

The above-mentioned hydrophilic macromolecule holds inorganic porous crystals in its inner matrix and forms the inorganic porous crystals-hydrophilic macromolecule composite to be used in the present invention. As used herein, by "in its inner matrix of hydrophilic macromolecule" is meant, when the hydrophilic macromolecule is a cellulose, for example, the inside of a substance constituting the cellulose. Fine pores and lumen present on the surface of the cell wall or in the cell wall of the cellulose are not included.

Having inorganic porous crystals in its inner matrix of cellulose means that a part or the entirety of the inorganic porous crystals is present in its inner matrix of the cellulose.

The inorganic porous crystals-hydrophilic macromolecule composite (A) can be prepared as in the following. In case of a zeolite-cellulose composite wherein the inorganic porous crystal is zeolite and the hydrophilic macromolecule is cellulose, for example, the method disclosed in Japanese Patent Unexamined Publication No. 8-245538 is used. To be specific, a cellulose substrate is immersed in a 1.0–100 mmol/l aqueous solution of silicon compound for 10 min to 2 hr and then in an aqueous solution of a mixture of 1.0–1000 mmol/l of an aluminum compound and 10–5000 mmol/l of a basic substance at 20–90° C. for 2 hr to 20 days.

When the hydrophilic macromolecule is pulp, cellophane or rayon, an inorganic porous crystals-pulp composite, an inorganic porous crystals-cellophane composite, and an inorganic porous crystals-rayon composite can be obtained by a method similar to the above-mentioned method.

The proportion of the inorganic porous crystals and hydrophilic macromolecule in the inorganic porous crystals-hydrophilic macromolecule composite (A) is not particularly limited. The inorganic porous crystals are preferably contained in (A) in a proportion of 1.0–70.0% by weight, particularly preferably 10.0–50.00%by weight.

Metal-holding Inorganic Porous Crystals-hydrophilic Macromolecule Composite

A metal-holding inorganic porous crystals-hydrophilic macromolecule composite can be obtained by immersing the above-mentioned inorganic porous crystals-hydrophilic macromolecule composite in an aqueous solution of a metal salt having a catalytic function. The metal to be used includes, for example, silver, copper, zinc, iron, nickel, cobalt, palladium, platinum and the like, which may be used in combination. While the concentration of the aqueous solution of a metal salt is not particularly limited, it is preferably 1.0–100 mmol/l, and the temperature and time of immersion are not particularly limited, either.

Inasmuch as the hydrophilic macromolecule permeates an aqueous solution, a metal can be held by the whole inorganic porous crystals in the inner matrix of the hydrophilic polymer.

While the content of the metal in the metal-holding inorganic porous crystals-hydrophilic macromolecule composite is not particularly limited, it is preferably 0.001–10.0 wt %, particularly preferably 0.01–1.0 wt %.

For example, the inorganic porous crystals-hydrophilic macromolecule composite holding silver, copper or zinc shows antibacterial properly, and the inorganic porous crystals-hydrophilic macromolecule composite holding palladium or platinum adsorbs ethylene. Thus, they are effective in retention of freshness of vegetables and fruits. The inorganic porous crystals-hydrophilic macromolecule composite holding silver or copper can adsorb or decompose hydrogen sulfide, so that it has an anticorrosion effect on a metal and deodorizing effect, as well as odor preventive effect based on absorption or decomposition of ammonium. Further, the inorganic porous crystals-hydrophilic macromolecule composite holding silver can adsorb and decompose methyl mercaptane, so that it is effective for odor prevention. In this case, since hydrophilic macromolecule can fully permeate gases, the entire metal-holding inorganic porous crystals in the inner matrix of the hydrophilic macromolecule can be utilized to adsorb or decompose gases.

Function Improver (B)

The composition of the present invention contains a member (B) for improving the functions such as strength and the like of a product obtained from this composition. The function improver (B) is preferably a carrier capable of solidifying. This carrier is not particularly limited as long as it can be solidified by some means after adding, to this carrier, an inorganic porous crystals-hydrophilic macromolecule composite (A) wherein the hydrophilic macromolecule contains inorganic porous crystals in its inner matrix. The means of solidifying may be, for example, heating, cooling, compression, chemical reaction (e.g., oxidation, enzyme reaction and the like), and the like. The degree of solidification may be such that it affords at least the production of a product, wherein said product may be one having bendability or may be deformable.

The carrier improves functions such as strength upon solidification that allows it to adhere to the composite (A).

Examples of such carrier include resin, inorganic hardener and the like. Examples of said resin include natural resin, synthetic resin, blends thereof and the like. Specific examples of natural resin include pine resin, shellac, wax, collagen, propolis, urushi, wood powder and the like. Synthetic resin may be, for example, polyolefin (e.g., polyethylene, polypropylene and the like), polyamide (e.g., polyacrylamide and the like), polyvinyl alcohol, phenol resin and the like. In addition, butadiene rubber, silicone rubber and the like can be also used. Preferred is polyethylene in view of price, low boiling point and general applicability. The blend of a natural resin and a synthetic resin can be obtained by a method known in the field of art. The mode of the carrier using a resin include, for example, a liquid (e.g., paint and the like), flexible one like rubber, board, sheet, string, net, cushion and the like.

The inorganic hardener includes, for example, cement, plaster, calcium carbonate, calcium silicate, titanium dioxide, zeolite, clay mineral, colloidal silica, apatite and talsite-like compound and the like.

Composition

The composition of the present invention can be produced by adding, to a function improver (B), an inorganic porous crystals-hydrophilic macromolecule composite (A) wherein hydrophilic macromolecule contains inorganic porous crystals in its inner matrix. To obtain a product, a flowable function improver, such as a paint, is applied to a composite (A) to be coated, which is followed by forming a film to give a product. A paint containing an acrylic resin is an emulsion, and evaporation of water therefrom results in a film. A paint containing an epoxy resin solidifies upon chemical reaction to give a product. The thickness of the product is 10–500 μm, preferably about 20–100 μm. The thickness of the product solidified using an inorganic hardener is about 1–10 cm. When the product is a sphere or ellipse, it has a long diameter of 0.1–5 cm, preferably 0.5–2 cm. A spherical product solidified using an inorganic hardener has the same size as above.

The shape of the composition after solidification is not particularly limited, and may be a sphere, cube, column, plate and the like.

The product obtained by solidification of the composition of the present invention and production method of the composition (liquid) of the present invention are explained in detail by referring to specific examples.

1. Production Method of Product Obtained by Solidification
    a. Plastic
    A zeolite-cellulose bead composite is added to a polyethylene master batch and the e is kneaded in a kneader set to 130° C. The kneaded product is extruded through a mold and cooled to solidify.
    b. Cement
    Commercially available cement is dissolved in water, to which titanium dioxide powder is added and the mixture is admixed, which is followed by addition of zeolite-pulp composite and further kneading. The mix is placed in a mold frame to allow generation of calcium silicate hydrate to give a solidified board.
    c. Film
    A zeolite-cellulose bead composite is dispersed in an acrylic or methacrylic resin paint and stirred. The mixture is applied to a plaster board or a plastic board with a brush or a roll After application to the board, water is evaporated to allow solidification to form a film.
    d. Fiber Board
    A wood powder obtained from a mil factory and a polyvinyl alcohol glue are mixed, to which zeolite-pulp composite is added and kneaded. The mixture is placed in a mold frame and pressurized and dried for solidification.
2. Production Method of a Fluid Such as Paint and the Like
    a. Thickener
    Carboxymethyl cellulose is dispersed in water and kneaded until it has appropriate viscosity (viscosity measured by a B type viscometer being about 100,000–1,000,000 centipoise), at which point a zeolite-cellulose bead composite is further added and kneaded.
    b. Polyvinyl Alcohol Glue
    Polyvinyl alcohol is dispersed in warm water at about 60° C. and kneaded until it has appropriate viscosity (viscosity measured by a B type viscometer being about 10,000–100,000 centipoise), at which point a zeolite-cellulose bead composite is further added and kneaded.
    c. Paint
    To a paint such as zinc iron board paint, zinc powder anticorrosive paint, acrylic resin paint, lead suboxide anticorrosive paint, acetyl cellulose transparent dope, oil varnish, amino alkyd resin paint, alkyd resin paint, aluminum paint, general anticorrosive paint, wood sealer, top coating, etching primer, enamel copper wire varnish, enamel paint, emulsion paint, oil primer, cashew resin paint, mold-resisting paint, volatile varnish, clear lacquer fluorescent paint, synthetic resin emulsion paint, synthetic resin paint, silicone resin paint, bleached shellac varnish, aqueous paint, purified urushi, shellac varnish, super varnish, cellulose lacquer, nitrocellulose lacquer, phenol resin paint, phthalic acid resin paint, unsaturated polyester resin paint, melamine resin paint and the like is added zeolite-cellulose bead composite, followed by kneading.

The proportion of the inorganic porous crystals-hydrophilic macromolecule composite (A) to be added is about 1–60 parts by weight per 100 parts by weight of the function improver (B). Where necessary, auxiliary agents such as surfactant, plasticizer, antioxidant, dispersant, precipitation preventive, wood filler, oil stain and the like may be added besides the function improver (B).

Textile, Nonwoven Fabric and Paper

Examples of the product of the present invention include a fiber (hereinafter also referred to as inorganic porous crystals-hydrophilic macromolecule composite fiber (A)) made from an inorganic porous crystals-hydrophilic macromolecule composite (A) wherein the hydrophilic macromolecule contains inorganic porous crystals in its inner matrix, and textile, nonwoven fabric and paper containing, as function improving fiber (B1), a fiber other than fiber (A).

Function Improving Fiber (B1)

The function improving fiber (B1) is a fiber other than composite fiber (A) and is free of inorganic porous crystals. It has an appropriate strength (e.g., one having a strength measured according to JIS L1069 "test method of tensile strength of fiber" of about 4–1500 gf/d, preferably about 20–500 gf/d).

Specific examples include at least one fiber selected from chemical fiber such as polyester fiber (e.g., polyethylene terephthalate), polyolefin fiber, polyurethane fiber, (poly) acrylic fiber, cellulose fiber (e.g., rayon, cupra and the like) and the like, natural fiber such as wool, silk, cotton, hemp, kenaf and the like, inorganic fiber such as glass fiber, carbon fiber, metal (e.g., copper, aluminum, iron, stainless and the like) fiber and the like, and active charcoal fiber. The above-mentioned chemical fiber may be made from a copolymer.

The fineness, sectional shape, presence or absence of various polymer stabilizers, basic weight, density and the like of the function improving fiber (B1) are not particularly limited.

Textile, Nonwoven Fabric or Paper

The textile, nonwoven fabric and paper of the present invention can be produced from an inorganic porous crystals-hydrophilic macromolecule composite fiber (A), and a function improving fiber (B1) according to a method known in the field of art. This textile includes mixed spinning textile, union cloth and the like depending on the kind of the yarns used for the warp and the woof of the textile. In view of the strength, a mixed spinning textile is preferable. The density and the like of the warp and the woof constituting the textile are not particularly limited.

The method for producing the nonwoven fabric include dry production method, wet production method and the like. In view of simplification of the production method and the kind of starting material, a dry production method is preferable. For example, when a thermoplastic resin such as polyethylene and the like is employed, a dry production method is preferable, and when a hydrophilic polymer such as pulp, rayon and the like is used, a wet production method is preferable, since a hydrogen bond is necessary.

Paper can be produced by a conventional paper making method (wet method and the like). For example, when the amount of pulp in the fiber (A) is large and fiber (B1) is a hydrophilic fiber, it is preferably produced by a wet method. When a fiber (B1) is hydrophobic fiber such as polyethylene and the like, and the hydrophobic fiber is used in an amount smaller than that of the pulp in the fiber (A), a wet method is preferable. In the latter case, each ingredient needs to be mixed well, and an additive for this end, such as surfactant and the like, can be added as necessary.

The proportion of the inorganic porous crystals-hydrophilic macromolecule composite fiber (A) and function improving fiber (B1) to be used is not particularly limited, and (A):(B) is preferably 10:90–90:10 by weight, particularly preferably 40:60–60:40 by weight.

The thickness of the textile, nonwoven fabric and paper of the present invention is about 20–500 μm, preferably 30–100 μm.

The textile, nonwoven fabric and paper of the present invention can contain, where necessary, additives such as polyacrylamide, starch and the like for enhanced paper strength, inorganic pigment for increased whiteness, and active charcoal, silica gel, hydrophobic zeolite, titanium dioxide and the like for improved multifunctions, and the like, besides the inorganic porous crystals-hydrophilic macromolecule composite fiber (A) and function improving fiber (B1).

Laminate

A different product of the present invention includes a laminate comprising a layer made from the inorganic porous crystals-hydrophilic macromolecule composite (A), wherein the hydrophilic macromolecule contains inorganic porous crystals in its inner matrix, and a function improving substrate (B2).

Substrate (B2)

The function improving substrate (B2) to be used in the present invention is exemplified by one having an appropriate strength (e.g., a strength measured according to JIS P8113 "test method of tensile strength of paper and paper board" of about 300–1000 gf, preferably about 500–750 gf, or a strength measured according to JIS L1069 "test method of tensile strength of fiber" of about 4–1500 gf/d, preferably about 20–500 gf/d) and other characteristics such as a good touch, weatherability, water resistance, heat insulating property, electromagnetic resistance and the like.

Specific examples include a sheet and the like of knit fabric, textile, nonwoven fabric and the like made from at least one fiber selected from natural fiber (e.g., wool, silk, cotton, hemp and the like), semisynthetic fiber (e.g., rayon, cupra and the like), synthetic fiber (e.g., polyethylene terephthalate polyester fiber, polyolefin fiber, polyurethane fiber, (poly)acrylic fiber and the like), metallic fiber (e.g., copper, aluminum and iron fibers and the like), inorganic fiber (e.g., glass fiber, carbon fiber and the like), and active carbon fiber, according to a method known in the field of the art. The above-mentioned synthetic fiber may be a copolymer, and the natural fiber and inorganic fiber may be a blend. The fineness, sectional shape, presence or absence of various polymer stabilizers, basic weight, density and the like of the sheet are not particularly limited.

The thickness of these sheet substrates is about 1–500 μm, preferably 10–100 μm.

The substrate (B2) to be used in the present invention is exemplified by, in addition to the sheet made from the above-mentioned fiber, a plastic film or sheet (hereinafter also referred to as a plastic film) made from a resin such as polyurethane, polyester, polyolefin, poly(vinyl chloride), poly(vinyl alcohol), polyacrylamide and the like, a regenerated cellulose film such as cellophane and the like, a metal foil made of copper, iron, aluminum, stainless and the like, a board and a sheet made from an inorganic hardener such as cement, plaster and the like, an inorganic membrane made from titanium dioxide, glass and the like, and the like can be also used.

When a good touch is desired for a substrate, the use of silk, rayon, cotton, hemp or kenaf is preferable, and when high weatherability and water resistance are desired, the use of a sheet or film made from a polyolefin resin such as polyethylene, polypropylene, polystyrene, polyethylene terephthalate and the like, aramid resin, polyacrylate resin or fiber, or inorganic membrane made from titanium dioxide, glass and the like is preferable, when high heat insulating property is desired, wool, polyacrylonitrile fiber, aluminum foil, foamed polyurethane and foamed polystyrene is preferable, and when high electromagnetic resistance is desired, the use of a metal (e.g., iron, aluminum, copper and the like) fiber or metal foil is preferable.

While the plastic film may be drawn or not drawn, a drawn one is preferable in view of strength. The method of drawing and drawing ratio are not particularly limited. This plastic film may be a foamed plastic film in view of heat insulating property and improved buffering property.

A foamed plastic film is produced by mixing a gas or a liquid capable of gasifying into a thermoplastic resin under pressurization, and heating or bringing to normal pressure, thereby to cause foaming, mixing a degradable foaming agent, heating to cause decomposition, thereby to cause foaming, or foaming with a gas generated during polymerization reaction, and other method. The expansion ratio is not particularly limited. Examples of foamed plastic include polystyrene foam, polyurethane foam and the like.

The thickness of the plastic film is about 10–500 $\mu$m, preferably 20–100 $\mu$m.

The regenerated cellulose film is exemplified by cellophane and the like. The thickness of the regenerated cellulose film is about 10–500 $\mu$m, preferably 20–100 $\mu$m.

The shape of the metal foil is not particularly limited. In view of strength, cost, weight, property and the like, however, a net is preferable. A method for forming a metal foil into a net structure includes a method which involves punching or processing once into a fiber before forming a net structure and the like.

The thickness of the metal foil is about 10–200 $\mu$m, preferably 20–100 $\mu$m.

The inorganic hardener includes, for example, cement, plaster, mastic, mortar, calcium silicate and the like. When an inorganic hardener is used as a substrate, the thickness thereof is 0.5–20 cm, preferably 1–10 cm.

The inorganic film is exemplified by glass, ceramics, titanium dioxide, zeolite and the like. The thickness of the inorganic film is 5–100 $\mu$m, preferably 10–50 $\mu$m.

The substrate (B2) to be used in the present invention contains at least one member selected from the sheets of the above-mentioned knit fabric, textile and nonwoven fabric and the like, a plastic film, a regenerated cellulose film, a metal foil, a sheet obtained from an inorganic hardener and an inorganic membrane.

A substrate is produced from two different kinds of materials, for example, polyethylene film and metal foil, or sheets of knit fabric, textile, nonwoven fabric and the like and a thermoplastic resin film, by superimposing the two different materials and passing them through a heat roll for thermal welding and other method. A method comprising forming an adhesive layer on a board made from plaster and adhering a polyurethane foam thereto may be used.

The thickness of the layer composed of an inorganic porous crystals-hydrophilic macromolecule composite varies depending on the purpose of use, which is preferably about 10–500 $\mu$m, and more preferably about 20–100 $\mu$m.

Figure 2:
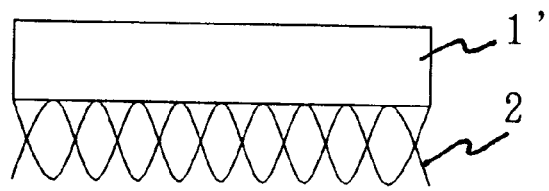
FIG. 2 shows another embodiment of the laminate of the present invention, wherein the inorganic porous crystals-hydrophilic macromolecule composite (A) is an inorganic porous crystals-pulp composite. In the FIG. 1' is a film-like substrate and 2 is a layer made from a fiber of the inorganic porous crystals-pulp composite.

A preferable embodiment of the laminate of the present invention wherein the inorganic porous crystals-hydrophilic macromolecule composite (A) is an inorganic porous crystals-pulp composite is shown in FIG. 1 and FIG. 2. In FIG. 1, 1 is a substrate, which is a collective fiber-like product and 2 is a layer made from an inorganic porous crystals-hydrophilic macromolecule composite (A), wherein the hydrophilic polymer is a collective fiber product.

In FIG. 2, 1' is a substrate, which is a film, 2 is a layer made from an inorganic porous crystals-hydrophilic macromolecule composite (A), which is a collective fiber product.

The laminate shown in FIG. 1 and FIG. 2 can be used mainly for shoji paper, fusuma paper, wall paper, curtain, rug, carpet, tapestry and the like.

Figure 3:
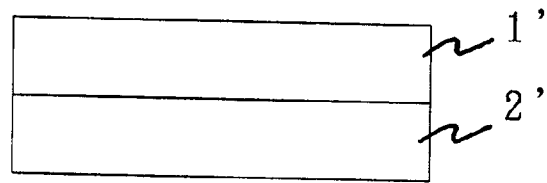
FIG. 3 shows a film-lie laminate of the present invention, wherein 2' is a film-like inorganic porous crystals-hydrophilic macromolecule composite.

The layer composed of an inorganic porous crystals-hydrophilic macromolecule composite (A) can take various shapes depending on the kind of the hydrophilic macromolecule to be used. For example, when the hydrophilic macromolecule is polyvinyl alcohol, crosslinked polyvinyl alcohol and the like, it can be a film. A preferable embodiment of the laminate of the present invention wherein the layer of the inorganic porous crystals-hydrophilic macromolecule composite (A) is a film which is shown in FIG. 3. In FIG. 3, 1' is a substrate film and 2' is a layer composed of an inorganic porous crystals-hydrophilic macromolecule composite (A), which is a film.

The laminate shown in FIG. 3 can be main used for freshness retaining sheet, anticorrosive sheet, insect preventive sheet, freshness retaining corrugated fibreboard, anticorrosive corrugated fibreboard, insect preventive corrugated fibreboard, fireproof corrugated fibreboard, and the like.

The thickness of the layer composed of an inorganic porous crystals-hydrophilic macromolecule composite (A), which is a film, is about 10–500 $\mu$m, preferably 20–100 $\mu$m.

Figure 4:
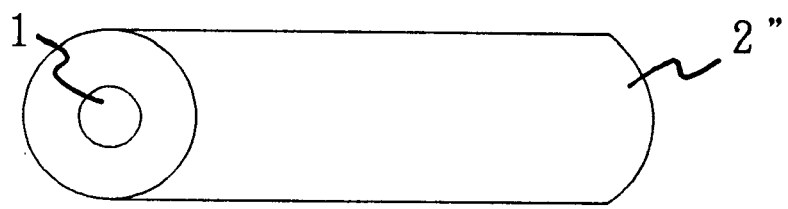
FIG. 4 shows a tube-like embodiment of the laminate of the present invention, wherein 2" is a tube-like layer made from an inorganic porous crystals-hydrophilic macromolecule composite fiber.

In the embodiment shown in FIG. 4, 2'' is a layer composed of an inorganic porous crystals-hydrophilic macromolecule composite (A), which is a tube and has a through-hole in the longitudinal direction, and 1 is a substrate which is filled in the through-hole. In the embodiment shown in FIG. 4, the hydrophilic macromolecule is a regenerated cellulose, and the substrate is a collective fiber. In this embodiment, the hydrophilic macromolecule is preferably a regenerated cellulose such as rayon and the like, and substrate 1 is preferably a sheet of a knit fabric, textile, nonwoven fabric and the like made from at least one member selected from plastic fiber made from polyolefin and the like, natural fiber and inorganic fiber such as metal fiber, glass fiber, carbon fiber and the like.

The laminate is mainly used for filter of air conditioner, dust bag of sweepers, filter for water tank of tropical fish, waste liquid filter and the like.

The sectional shape in the direction of the center of the through-hole is complete round, ellipse, rectangle and the like. When it is a complete round, its diameter is about 1–100 $\mu$m; when it is an ellipse, the length of the longer axis is about 2–100 $\mu$m, the length of the shorter axis is about 1–50 $\mu$m; sectional area thereof is generally 0.79–7900 $\mu m^2$, preferably 2000 $\mu m^2$. The longitudinal length of the composite is about 1–200 $\mu$m and the length in the transverse direction is about 5–1000 $\mu$m.

Figure 5:
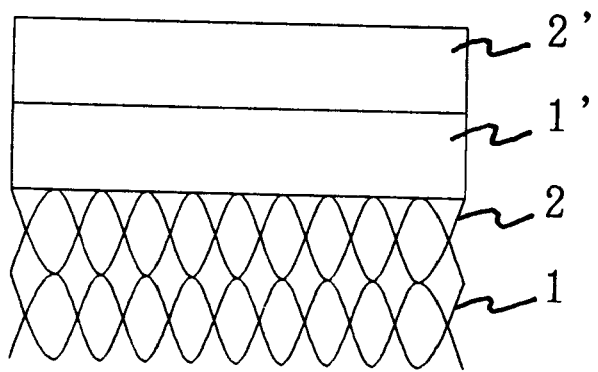
FIG. 5 shows an embodiment of a sheet of the laminate of the present invention.

FIG. 5 shows an embodiment wherein a laminate of FIG. 3 is superimposed on the laminate of FIG. 1. The substrate 1 is preferably a nonwoven fabric made from a natural fiber. The layer composed of the inorganic porous crystals-hydrophilic macromolecule composite (A) is preferably a zeolite-pulp composite layer. The substrate 1' is preferably a plastic film, particularly polyvinyl alcohol copolymer film; the layer 2' made from an inorganic porous crystals-hydrophilic macromolecule composite is preferably a zeolite-cellophane composite layer.

The thickness of this composite layer is preferably not more than 500 $\mu$m, in view of formability into a box or honeycomb, and portable property.

The laminate shown in FIG. 5 is mainly used for portable toilet for automobile, paper diaper, water purification device for survival and the like.

The layer composed of the inorganic porous crystals-hydrophilic macromolecule composite (A) contains a volatile substance besides the above-mentioned inorganic porous crystals-hydrophilic macromolecule composite (A) to achieve high functions. Examples of the volatile substance include L-menthol, hinokitiol, fitontsid, allyl isothiocyanate, limonene and the like. These can be held by a method known in the art, such as immersion, coating, press incorporation and the like.

The laminate of the present invention can be produced by the following method. When the substrate (B2) is a sheet made from the above-mentioned fiber and the hydrophilic macromolecule of the inorganic porous crystals-hydrophilic macromolecule composite (A) is pulp, the substrate (B2) and the sheet of the inorganic porous crystals-hydrophilic macromolecule composite (A) are welded to give a laminate.

When the substrate (B2) is other than the above-mentioned sheet, a layer made from the inorganic porous crystals-hydrophilic macromolecule composite (A) is adhered to at least one surface of the substrate (B2) with an adhesive, or a layer made from the inorganic porous crystals-hydrophilic macromolecule composite (A) is adhered while an inorganic hardener, such as cement, plaster and the like, has not solidified yet, with an adhesive and the like to give a laminate. The thickness of the adhesive layer is about 5–100 $\mu$m, preferably 10–50 $\mu$m.

In the embodiment wherein the inorganic porous crystals-hydrophilic macromolecule composite (A) has a through-hole in the longitudinal direction, this through-hole may be filled with a substrate or applied to a regeneration bath while a viscose attaches to the periphery of the substrate or other method.

The laminate of the present invention can be further laminated with, besides substrate (B2) and a layer made from the inorganic porous crystals-hydrophilic macromolecule composite (A), for example, a sheet such as a knit fabric, textile, nonwoven fabric and the like, which is made from a natural fiber having hydrophilicity and gas permeability. The thickness of this layer is approximately the same as that mentioned above.

When an inorganic porous crystals-hydrophilic macromolecule composite (A) wherein the hydrophilic macromolecule contains inorganic porous crystals in its inner matrix and a function improver (B) or function improving fiber (B1) are combined, or when a layer made from an inorganic porous crystals-hydrophilic macromolecule composite (A) wherein the hydrophilic polymer contains inorganic porous crystals in its inner matrix is laminated on a function improving substrate (B2), the product, textile, nonwoven fabric, paper and laminate obtained from the composition of the present invention come to have high strength, in addition to the gas adsorption capability, volatile organic solvent removing capability, noncombustibility, heat insulating property, and heavy metal and radioactive element removing capability, that the inorganic porous crystals-hydrophilic macromolecule composite (A) has. It is also possible to improve a touch such as texture and the like, hydrophilicity, water repellency, anticorrosive property and the like according to the fraction improvers (B), (B1) and (B2) to be used. Therefore, the inventive laminate can be used for various applications such as underwear, bath mat, sheets, gloves, pillow cover, stuffing cotton for pillow, bedding, padded sleeveless coat, cushion and the like, shod paper, wall paper, clothes cover, cushion cover, bedding storage bag, insecticide sheet, pack for vacuum cleaner, filter for air conditioners, filter for air purifier, scrubbing brush for tableware, water draining garbage bag, carpet, hot carpet cover, curtain, deodorant sheet for refrigerator, special filter paper, freshness retention sheet for vegetable, meat and the like, packaging materials for freshness retention transport, wall materials, floor materials, ceiling materials, dewing absorption sheet and the like.

Particularly, the use of a metal-holding inorganic porous crystals-hydrophilic macromolecule composite wherein the inorganic porous crystals-hydrophilic macromolecule composite to be used in the present invention carries a metal such as silver, copper, zinc and the like can impart the properties of antibacterial property, odor removing capability and the like, in addition to the above-mentioned properties. Therefore, the inventive laminate can be also used for various applications such as paper diapers, diaper cover, portable toilet for automobile, insole, artificial leather, decoration of automobile, train, airplane, ship and the like (seat, seat cover), towel, toilet seat cover, and the like.

The present invention is explained in the following by way of examples, to which the present invention is not limited.

PRODUCTION EXAMPLE 1

Cellulose beads (10.0 g, average particle size 5 mm) which are molded particles of regenerated cellulose were impregnated with an aqueous solution of sodium methasilicate 9 hydrate (5.68 g/100 ml) and a mixed aqueous solution (100 ml) of sodium aluminate (4.68 g) and sodium hydroxide (10.00 g) was added, which was followed by immersion at 25° C. for 10 days to give 11.2 g of zeolite-cellulose bead composite. The zeolite-cellulose bead composite had a zeolite-holding percentage of 20.8 wt %.

EXAMPLE 1

The zeolite-cellulose bead composite obtained in Production Example 1 was added to cement for general building materials dispersed with colloidal silica and titanium dioxide, and the mixture was homogeneously kneaded. The kneaded product was placed in a mold and left standing to give a product (thickness 3.0 cm).

EXPERIMENTAL EXAMPLE 1

The product obtained in Example 1 was cut out in squares of one side 10 cm×10 cm and used as test pieces. The test piece was placed in a bag (3.0 L content) made of a film having high gas barrier property and the air inside was removed once. A 100 ppm nitrogen dioxide gas (3.0 L) and the test piece was sealed therein and placed at 30 cm under a 15 W fluorescent lamp. Similarly, a 100 ppm ammonium gas (3.0 L) and the test piece were sealed in a bag prepared in a similar manner and placed at 30 cm under a 15 W fluorescent lamp. As a comparative test beads, zeolite-cellulose bead composite (10 g) was used and, as a comparative test piece No. 2, a test piece having the same shape and obtained by dispersing colloidal silica and titanium dioxide in cement for general building materials was used. The nitrogen dioxide gas concentrations inside were measured with the lapse of time, the results of which are shown in FIG. 6. The ammonia gas concentrations inside were measured with the lapse of time, the results of which are shown in FIG. 7. As shown in FIG. 6 and FIG. 7, the product obtained in Example 1 showed most superior gas removing capability of nitrogen dioxide gas and ammonia gas.

PRODUCTION EXAMPLE 2

Pulp (200 g) was impregnated with an aqueous solution of sodium methasilicate 9 hydrate (190 g/5000 ml) and a mixed aqueous solution (5000 ml) of sodium aluminate (150 g) and sodium hydroxide (330 g) was added, which was followed by immersion at 90° C. for 2 hr to give 290 g of zeolite-pulp composite. The zeolite-pulp composite had a zeolite-holding percentage of 38.0 wt %.

EXAMPLE 2

The zeolite-pulp composite (100 g) obtained in Production Example 2 was mixed with wood powder (300 g), polyvinyl alcohol, vinyl acetate adhesive (50 g) and water (200 g), and the mixture was placed in a mold and pressurized to give a product (thickness 3.0 cm).

EXPERIMENTAL EXAMPLE 2

The product obtained in Example 2 was cut out in squares of one side 10 cm×10 cm and used as test pieces. The test piece was placed in a bag (3.0 L content) made of a film having high gas barrier property and the air inside was removed once. A 100 ppm ammonium gas (3.0 L) was sealed therein. A wood board of the same shape obtained in the same manner as above except that the zeolite-pulp composite was not used was used as comparative test piece No. 3. The ammonia gas concentrations inside were measured with the lapse of time, the results of which are shown in FIG. 8. As shown in FIG. 8, the wood board prepared as comparative test piece scarcely adsorbed ammonia gas, whereas the product obtained in Example 2 showed superior gas removing capability of ammonia gas.

EXAMPLE 3

A paper (basic weight 100 g/m$^2$, paper width 50 cm) was made from the zeolite-pulp composite obtained in Production Example 2. The paper was impregnated with a copolymer of phenol resin (novolac) and hexamethylene tetramine, which copolymer is used as an undercoating. Excess resin was scraped off to make the total thickness (paper thickness) 100 μm. Ten minutes later, phenol resin cured, whereby a product was obtained.

EXPERIMENTAL EXAMPLE 3

The product obtained in Example 3 was cut out in squares of one side 10 cm×10 cm and used as test pieces. The test piece was immersed in an aqueous solution (100 cm$^3$) of silver nitrate adjusted to 10 ppm and, 30 minutes later, the silver concentration of this aqueous solution was measured and found to be 50 ppb. The test piece noticeably reduced the silver concentration.

EXAMPLE 4

Zeolite-pulp composite (100 g) obtained in Production Example 2 was impregnated with an aqueous solution of calcium chloride (0.30 mmol/1000 ml) and this zeolite was changed to 5A zeolite having larger pore size. To the 5A zeolite-pulp composite (10.0 g) were added collagen (5.0 g) and calcium phosphate (1.0 g) to give a molded product (5 cm×3 cm×1 cm).

EXPERIMENTAL EXAMPLE 4

The product (5 cm×3 cm×1 cm) obtained in Example 4 was immersed in an artificial body fluid (100 cm$^3$) and preserved at 38° C. Thirty days later, the product was taken out and dried, and dry weight was measured. The weight was 15.8 g when first measured but 30 days later, the weight increased to 16.5 g. The surface at the beginning of the test was smooth, but gritty 30 days later due to generation of artificial bone. The calcium and phosphorus concentrations of the artificial body fluid were measured, which were found to be 30% less than the concentrations at the beginning of the test.

EXAMPLE 5

Untreated pulp (450 g) was added to the zeolite-pulp composite (200 g) obtained in Production Example 1 and the mixture was placed in a chest. Water (65 L) was added to make the pulp slurry concentration 1 wt % and the mixture was stirred for 1 hour. This mixed pulp slurry was applied to an inclined wire-netting paper making machine (angle of inclination 5°, rate 10 m/min) to make a paper (basic weight 100 g/m$^2$, paper width 50 cm).

COMPARATIVE EXAMPLE 1

Water (20 L) was added to the zeolite-pulp composite (200 g) obtained in Production Example 2 to make the pulp slurry concentration 1% and the mixture was stirred for 1 hour. This mixed pulp slurry was applied to an inclined wire-netting paper making machine (angle of inclination 5°, rate 10 m/min) to make a paper (basic weight 100 g/m$^2$, paper width 50 cm).

EXPERIMENTAL EXAMPLE 5

The papers obtained in Example 5 and Comparative Example 1 were tested for the compression strength in the CD direction according to JIS P8126, tensile strength in the CD direction according to JIS P8113, tear strength in the CD direction according to JIS P8116, and burst strength in the CD direction according to JIS P8112.

The results are shown in Table 1. In the Table, the unit of the compression strength and tensile strength is kgf, the unit of the burst strength is kgf/cm$^2$, and the unit of tear strength is gf.

TABLE 1

| | Compression strength | Tensile strength | Tear strength | Burst strength |
|---|---|---|---|---|
| Example 5 | 7.0 | 2.2 | 230 | 2.5 |
| Comparative Example 1 | 2.0 | 0.5 | 30 | 1.3 |

The paper of Example 5 was superior to the paper of Comparative Example 1 in every strength test. This is attributable to the stronger hydrogen bond in the paper of Example 5 than in the paper of Comparative Example 1.

PRODUCTION EXAMPLE 3

Pulp (300 g) was impregnated with an aqueous solution of sodium methasilicate 9 hydrate (190 g/5000 ml) and a mixed aqueous solution (5000 ml) of sodium aluminate (150 g) and sodium hydroxide (330 g) was added, which was followed by immersion at 90° C. for 2 hr to give a zeolite-pulp composite. The zeolite-pulp composite thus obtained had a zeolite-holding percentage of 30.1 wt %.

This zeolite-pulp composite was applied to an inclined wire-netting paper making machine (angle of inclination 50°, rate 10 m/min) to make a zeolite-holding paper (basic weight 100 g/m$^2$, paper width 50 cm).

EXAMPLE 6

A rayon nonwoven fabric (basic weight 60 g/m$^2$, cloth width 50 cm) prepared by wet method was adhered to the zeolite-holding paper obtained in Production Example 3 using a starch clue as a binder, whereby a laminate was obtained.

EXAMPLE 7

The zeolite-holding paper obtained in Production Example 3 was passed trough a thermal roll and heated to make the surface temperature 150° C. A nonwoven fabric (thickness 30 μm) made from a polyethylene-polypropylene composite fiber prepared by dry method was continuously brought into contact therewith while spraying an absorbing polymer powder, to give a laminate.

EXAMPLE 8

The zeolite-holding paper obtained in Production Example 3 was passed through a thermal roll and heated to make the surface temperature 150° C. This step was done in two series and a low density polyethylene (LDPE film, thickness 40 μm, width 50 cm) was continuously brought into contact with the papers by placing the polyethylene between them, whereby a laminate was obtained, which carried LDPE film between these zeolite-holding papers upon heat-melting.

EXAMPLE 9

The zeolite-holding paper obtained in Production Example 3 was passed through thermal roll and heated to make the surface temperature 150° C. This step was done in two series and a polyethylene nonwoven fabric (thickness 30 μm) obtained by dry method was continuously brought into contact with the papers by placing the fabric between them, whereby a laminate was obtained, which carried polyethylene nonwoven fabric between these zeolite-holding papers upon heat-melting.

PRODUCTION EXAMPLE 4

Cellophane (200 g) was impregnated with an aqueous solution of sodium methasilicate 9 hydrate (190 g/5000 ml) and a mixed aqueous solution (5000 ml) of sodium aluminate (150 g) and sodium hydroxide (330 g) was added, which was followed by reaction for 4 hr in a steam generator wherein steam (110° C.) was generated to give zeolite-cellophane composite. The zeolite-cellophane composite had a zeolite-holding percentage of 15.3 wt %.

EXAMPLE 10

The zeolite-cellophane composite obtained in Production Example 4 was passed through a thermal roll and heated to make the surface temperature 150° C. This step was done in two series and LDPE film (thickness 40 μm, width 50 cm) was continuously brought into contact with the two cellophanes by placing the film between them, whereby a laminate was obtained, which carried LDPE film between the holding cellophane upon heat-melting.

EXAMPLE 11

The laminate (15.0 g) obtained in Example 10 was immersed in an aqueous solution (500 ml) of copper sulfate 5 hydrate (2.20 g) for 2 hours, whereby a copper (5.0 mmol)-holding laminate was obtained.

EXAMPLE 12

A high strength rayon fiber (100 g) comprising rayon and polypropylene, polypropylene being inserted into the core section of the rayon fiber when regenerating the rayon, and having polypropylene (core diameter 20 μm; fineness 50 μm; average fiber length 20 mm) was impregnated with an aqueous solution of sodium methasilicate 9 hydrate (85 g/2000 ml) and a mixed aqueous solution (2000 ml) of sodium aluminate (80 g) and sodium hydroxide (160 g), which was followed by immersion at 90° C. for 2 hr to give a zeolite-rayon composite fiber having the shape shown in FIG. 4. This zeolite-rayon composite fiber was highly strong and zeolite has been present only in the rayon section. The zeolite-rayon composite fiber had a zeolite-holding percentage of 23.5 wt %.

EXAMPLE 13

A nonwoven fabric produced from the zeolite-rayon composite fiber obtained in Example 12 by a wet method, and a polyethylene nonwoven fabric prepared by a dry method were heat treated in the same manner as in Example 8, brought into contact with each other and melt-adhered. Then, a sheet made from an active charcoal fiber by a dry method was brought into contact therewith and melt-adhered to give a three-layer laminate.

EXAMPLE 14

A foamed polyurethane sheet (thickness 10 mm) was adhered to the laminate obtained in Example 9 via a vinyl acetate resin emulsion adhesive and an aluminum foil (thickness 10 μm) was adhered thereto, whereby a 4-layer laminate shown in FIG. 5 was obtained.

EXAMPLE 15

Wall mortar (1 kg) was dissolved in water (1 L) and poured into a mold (25 cm×25 cm×5 cm) made of an acrylic plate (thickness 5 mm). When this mortar became half dry, the zeolite-holding paper prepared in Production Example 3 was placed thereon, which was allowed to stand to complete dryness. The mold was removed and colloidal silica containing titanium dioxide dispersed therein was applied to a plane opposite to the plane, to which the zeolite-holding paper had been adhered, to the thickness of 50 μm, whereby a laminate was obtained.

The above-mentioned laminate obtained in Example 6 is superior in surface appearance and a touch and can remove bad smells, so that it is preferably used as a material for wall paper. The laminate obtained in Example 7 is preferably used as a deodorant sheet for paper diapers, sanitary items, and the like. The laminate obtained in Example 8 is preferably used as a freshness retaining sheet for fruits and vegetables. The laminate obtained in Example 9 is preferably used as a gaseous or liquid phase filter, since it has high strength and superior gas permeability by sandwiching a polyethylene nonwoven fabric between two sheets of zeolite-holding paper. The laminates obtained in Examples 12 and 13 are also preferably used as a gaseous or liquid phase filter as in Example 9. In particular, the laminate obtained in Example 13 adsorbs not only polar molecules but also nonpolar molecules, which makes it useful as a gaseous phase filter.

The laminate obtained in Example 10 is preferably used as a cation exchange sheet, and the laminate obtained in Example 11 is preferably used as an antibacterial sheet since it exerts antibacterial property due to copper ion.

The laminate obtained in Example 14 is preferably used as a building panel material, since it is superior in heat insulation, buffering and electromagnetic resistance, adsorbs abnormally smelling gases, and has high strength. The laminate obtained in Example 15 is also preferably used as a building panel material as in Example 14, and exhibits optical catalyst function due to titanium dioxide.

When an inorganic porous crystals-hydrophilic macromolecule composite (A) wherein the hydrophilic macromolecule composite contains inorganic porous crystals in its inner matrix and a function improver (B), function improving fiber (B1) or function improving substrate (B2) are combined, the product, textile, nonwoven fabric, paper and laminate obtained from the composition of the present invention come to have high strength, in addition to the gas adsorption capability, volatile organic solvent removing capability, noncombustibility, heat insulating property, and heavy metal and radioactive element removing capability, that the inorganic porous crystals-hydrophilic macromolecule composite (A) possesses. It is also possible to improve a touch and the like, so that the composition is useful as a material having additional functions. By making an inorganic porous crystal hold a metal, a composition, product, textile, nonwoven fabric, paper and laminate further having antibacterial properly and bad smell removing capability and the like can be provided.

What is claimed is:

1. A composition comprising (A) an inorganic porous crystals-hydrophilic macromolecule composite, wherein the hydrophilic macromolecule contains 1–70 wt. % inorganic porous crystals in its inner matrix, and wherein the hydrophilic macromolecule is at least one member selected from the group consisting of natural cellulose, regenerated cellulose, bacterial cellulose, silk, wool, hemp, chitin, collagen, propolis, urushi, and wood powder, and (b) a carrier that is solid or solidifies.

2. The composition of claim 1, wherein the carrier (B) is a carrier that solidifies.

3. A product obtained by solidifying the composition of claim 2.

4. The composition of claim 1, wherein the inorganic porous crystals of the inorganic porous crystals-hydrophilic macromolecule composite (A) are zeolite.

5. The composition of claim 1, wherein the inorganic porous crystals comprise at least one metal selected from the group consisting of silver, copper, zinc, iron, nickel, cobalt, palladium and platinum.

6. The composition of claim 1, wherein the natural cellulose is at least one member selected from the group consisting of pulp, cotton, hemp and kenaf.

7. A product comprising (A) an inorganic porous crystals-hydrophilic macromolecule composite wherein the hydrophilic macromolecule contains 1–70 wt. % inorganic porous crystals in its inner matrix, and wherein the hydrophilic macromolecule is at least one member selected from the group consisting of natural cellulose, regenerated cellulose, bacterial cellulose, silk, wool, hemp, chitin, collagen, propolis, urushi, and wood powder, and (B) a carrier that is solid or solidifies.

8. The product of claim 7, which is a laminate comprising a layer made from the inorganic porous crystals-hydrophilic macromolecule composite (A) and a carrier substrate (B2).

9. The product of claim 8, wherein the carrier substrate (B2) comprises at least one member selected from the group consisting of a plastic film, a regenerated cellulose film, a metal foil, a natural fiber, a semisynthetic fiber, a synthetic fiber, a metallic fiber, an inorganic fiber, an active charcoal fiber, an inorganic hardener and an inorganic membrane.

10. The product of claim 7, which is a textile, nonwoven fabric or paper comprising a fiber made from the inorganic porous crystals-hydrophilic macromolecule composite (A) and a carrier fiber (B1).

11. The product of claim 10, wherein the carrier fiber (B1) comprises at least one member selected from the group consisting of a natural fiber, a semisynthetic fiber, a synthetic fiber and an inorganic fiber.

12. The product of claim 7, wherein the inorganic porous crystals are zeolite.

13. The product of claim 7, wherein the inorganic porous crystals comprise at least one metal selected from the group consisting of silver, copper, zinc, iron, nickel, cobalt, palladium and platinum.

14. The composition of claim 7, wherein the natural cellulose is at least one member selected from the group consisting of pulp, cotton, hemp and kenaf.

* * * * *

UNITED STATES PATENT AND TRADEMARK OFFICE
CERTIFICATE OF CORRECTION

PATENT NO.    : 6,372,333 B1
DATED         : April 16, 2002
INVENTOR(S)   : Sugiyama et al.

It is certified that error appears in the above-identified patent and that said Letters Patent is hereby corrected as shown below:

<u>Title page,</u>
Item [56], References Cited, FOREIGN PATENT DOCUMENTS,
Third reference, "WO    WO 92/16291     10/1992" should read as
-- WO        92/16291       10/1992 --.

Item [57], ABSTRACT,
Line 5, "therefrom The" should read -- therefrom. The --.

<u>Column 17,</u>
Line 32, "(b)" should read -- (B) --.

Signed and Sealed this

Fifth Day of November, 2002

Attest:

JAMES E. ROGAN
*Attesting Officer*           *Director of the United States Patent and Trademark Office*